(12) United States Patent
Baillargeon et al.

(10) Patent No.: US 6,887,221 B1
(45) Date of Patent: May 3, 2005

(54) CONNECTOR FOR IRRIGATION-ASPIRATION INSTRUMENT

(75) Inventors: Jean-Martin Baillargeon, Kirkland, WA (US); Michael A. Stoy, Bothell, WA (US); Lawrence Laks, Bellevue, WA (US)

(73) Assignee: MicroSurgical Technology, Inc., Redmond, WA (US)

( * ) Notice: Subject to any disclaimer, the term of this patent is extended or adjusted under 35 U.S.C. 154(b) by 47 days.

(21) Appl. No.: 10/325,482

(22) Filed: Dec. 18, 2002

Related U.S. Application Data (60) Provisional application No. 60/341,975, filed on Dec. 18, 2001.

(51) Int. Cl.$^7$ .................. A61M 5/00; A61M 31/00; A61B 17/20; A61B 17/22; A61F 9/00
(52) U.S. Cl. .................. 604/181; 604/521; 604/22; 606/107; 606/159
(58) Field of Search .................. 604/22, 181, 43–48, 604/521, 294, 290, 289, 291, 37, 25, 27, 604/107, 180, 183, 520, 101.05, 19; 606/196, 606/159, 128, 439, 107, 169

(56) References Cited

U.S. PATENT DOCUMENTS

| | | |
|---|---|---|
| 4,580,816 A | 4/1986 | Campbell et al. |
| 4,619,640 A | 10/1986 | Potolsky et al. |
| D321,251 S | 10/1991 | Jepson et al. |
| 5,162,044 A * | 11/1992 | Gahn et al. .................. 604/22 |
| D380,037 S | 6/1997 | Grantham |
| 5,676,649 A | 10/1997 | Boukhny et al. |
| 5,885,243 A | 3/1999 | Capetan et al. |
| 6,254,587 B1 * | 7/2001 | Christ et al. ................ 604/521 |
| 6,406,470 B1 | 6/2002 | Kierce |

* cited by examiner

Primary Examiner—Nicholas D. Lucchesi
Assistant Examiner—Roz Maiorino
(74) Attorney, Agent, or Firm—Christensen O'Connor Johnson Kindness PLLC (57) ABSTRACT

A medical instrument includes a handpiece having irrigation and aspiration channels, a connector coupled to the handpiece by a sliding friction fit and having channels forming continuations of the irrigation and aspiration channels, and a removable tip threadedly coupled to the connector.

9 Claims, 12 Drawing Sheets

CONNECTOR FOR IRRIGATION-ASPIRATION INSTRUMENT

CROSS-REFERENCE TO RELATED APPLICATION

This application claims the benefit of U.S. Provisional Application No. 60/341,975, filed on Dec. 18, 2001.

FIELD OF THE INVENTION

The present invention relates to medical devices, but in particular to irrigation-aspiration (I/A) devices such as those used during cataract surgery.

BACKGROUND OF THE INVENTION

One of the more common afflictions to affect aging eyes are cataracts, which cause gradually deteriorating vision. Advances in ophthalmic surgery allow many cataracts to be removed and vision restored.

Treating cataracts typically involves the removal of the clouded natural lens and replacement with an artificial lens. Removal of the lens requires an incision or tunnel to be made in and/or adjacent to the cornea. The tip portion of a phaco emulsifier is inserted through the incision and vibrates ultrasonically to liquefy the lens. The emulsified lens is removed from the lens capsule by aspiration. Modern aspirators also perform irrigation. I/A instruments have dual passages, one for irrigation and the other for aspiration. Usually the passages are coaxial, the inner passage being formed by a rigid or semi-rigid cannula, and the outer passage having a distal portion formed by a sleeve which may be resilient. One or more components of the tips are removable from the handpiece of the instrument for selection of an appropriate or desired tip, and for replacement of the tip.

SUMMARY OF THE INVENTION

The present invention provides a connector or adapter that allows an I/A handpiece of one design to receive tip components of different designs. For example, an I/A handpiece of one manufacturer may be designed with a connection system to receive tip components of that manufacturer. By use of the present invention, the handpiece may be used with tip components of another manufacturer, from an I/A system having a different interconnection with a handpiece. Therefore, the user need not rely on the availability of I/A tips having connection systems specifically designed for a particular I/A handpiece. Rather, if desirable features are available from other manufacturers, the present invention allows such tips to be reliably fitted on existing handpieces.

In representative embodiments, connectors or adapters in accordance with the present invention may have a proximate stem adapted for a sliding friction fit with a handpiece, and a distal end designed for a threaded interconnection with an aspiration tip.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENTS

Figure 1:
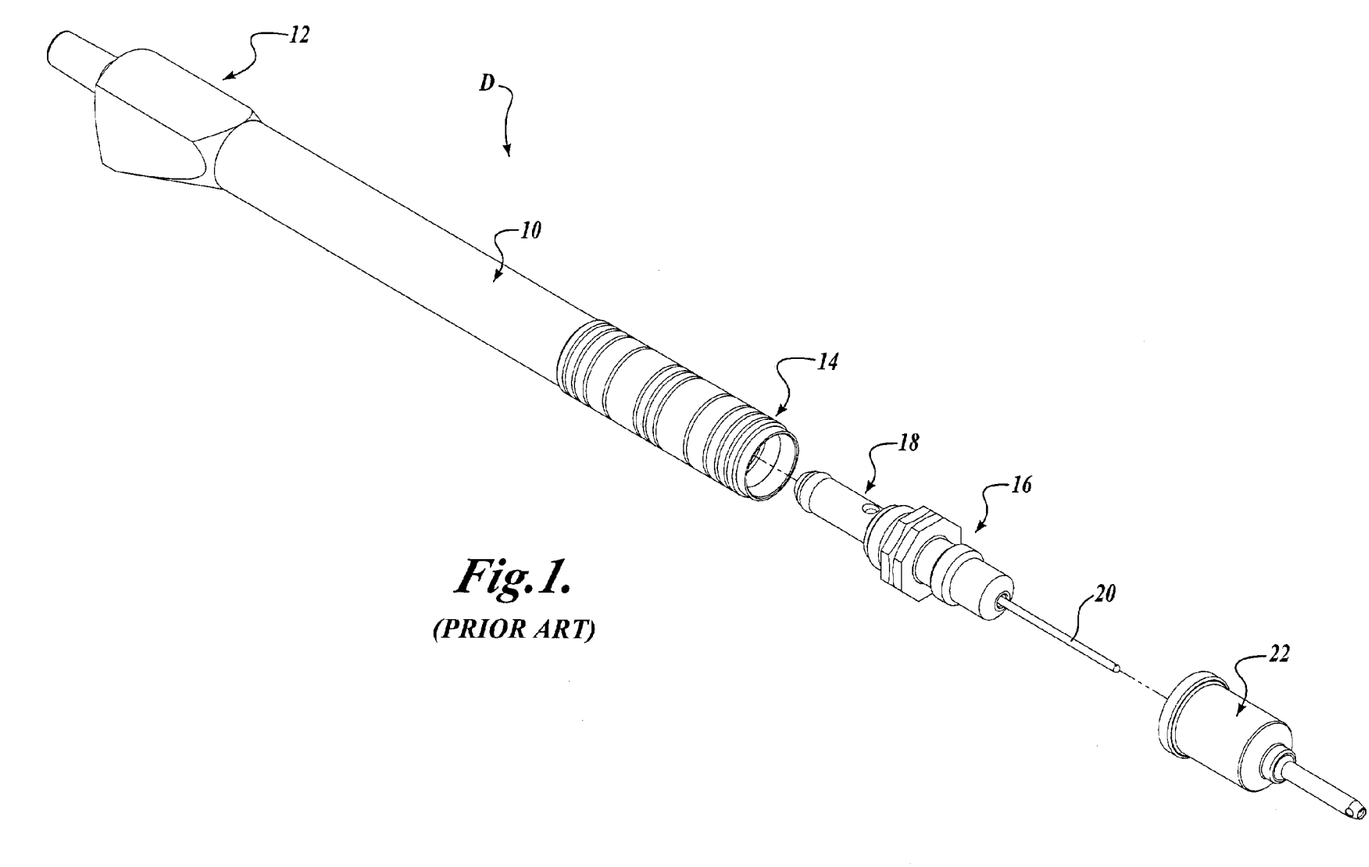
FIG. 1 (Prior Art) is a top perspective of a known I/A instrument with parts shown in exploded relationship.
Figure 2:
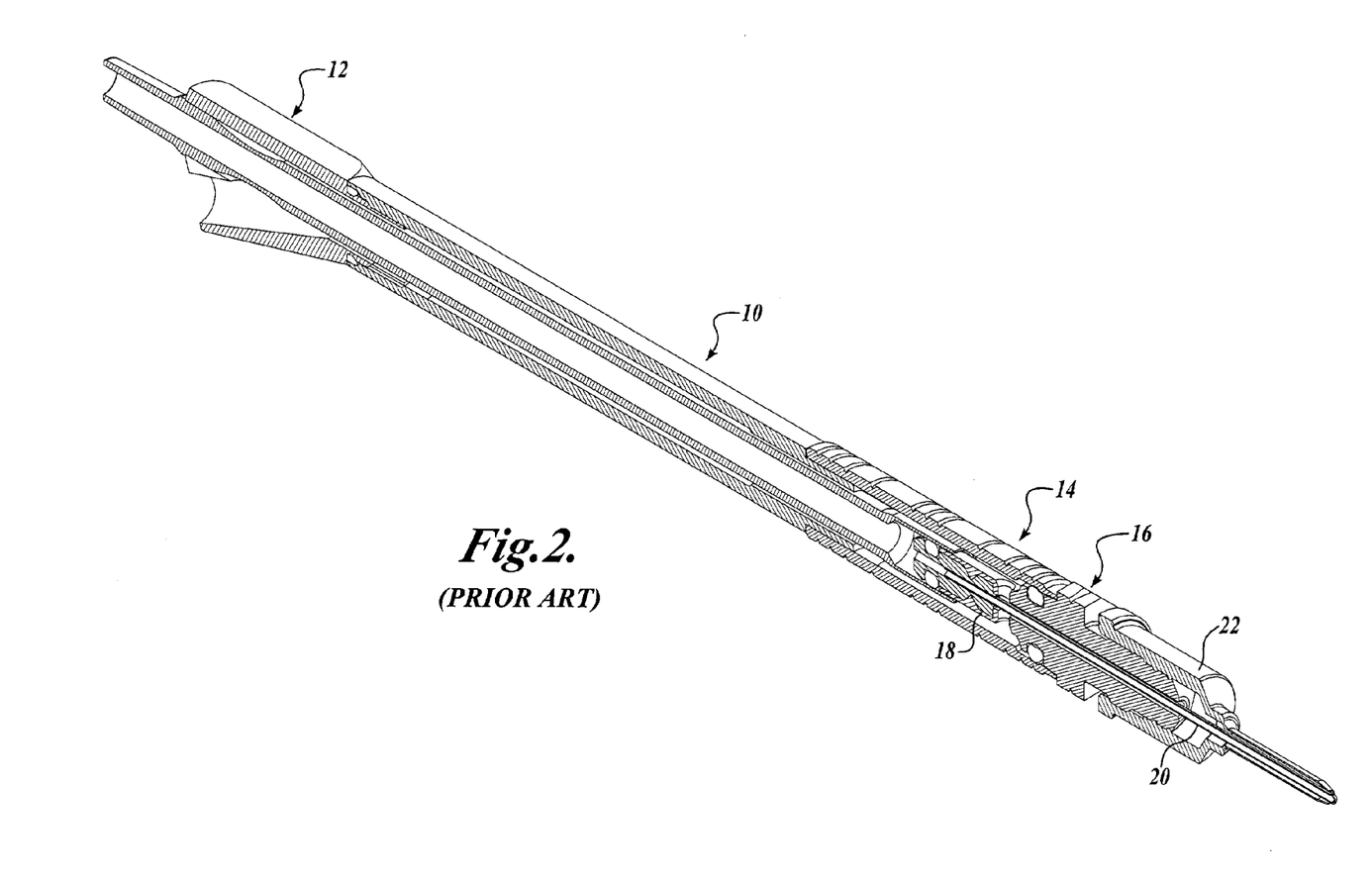
FIG. 2 (Prior Art) is a corresponding top perspective of the instrument of FIG. 1 with parts assembled and shown in section.
Figures 3, 4:
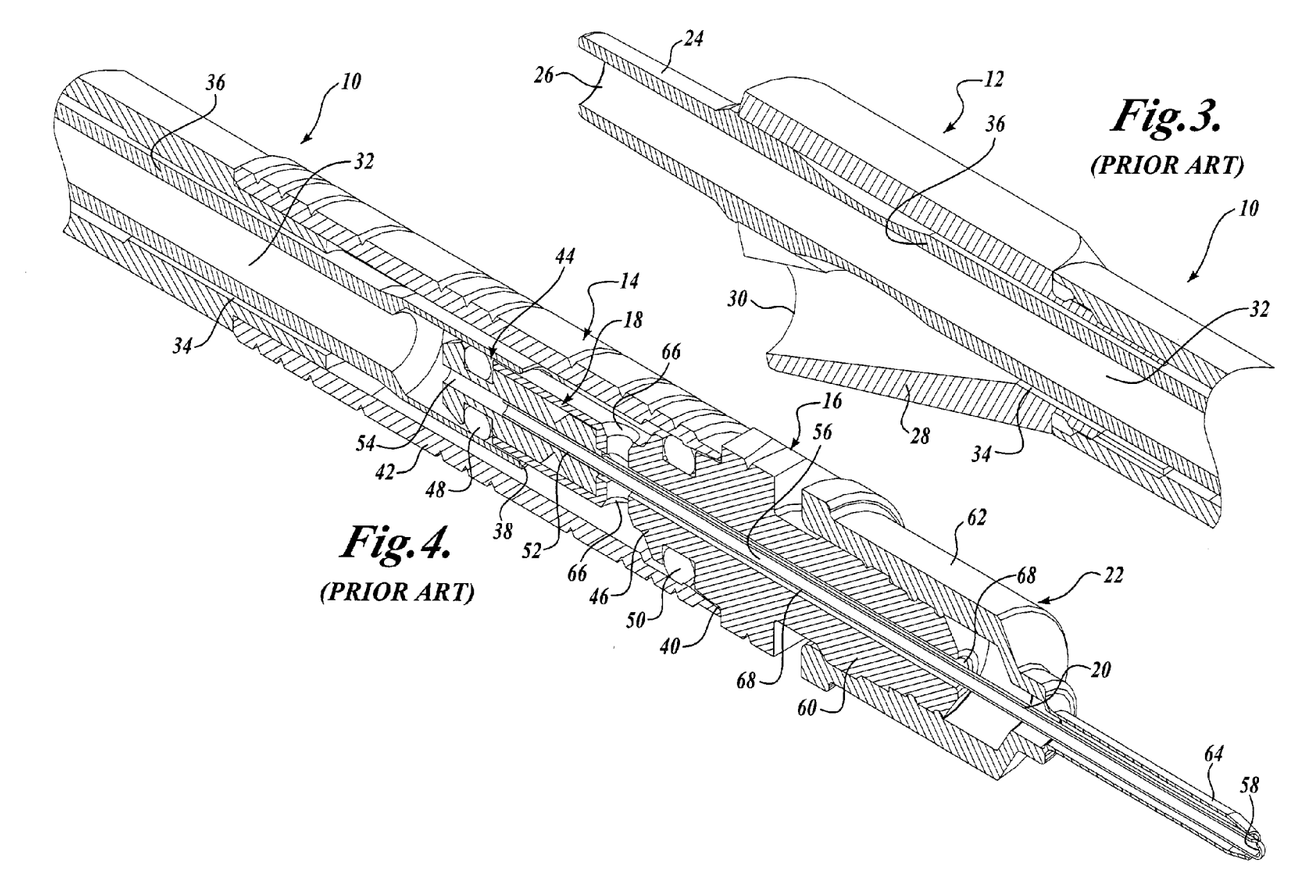
FIG. 3 (Prior Art) is an enlarged, fragmentary, perspective detail of the proximate end portion of the known instrument of FIGS. 1 and 2.
FIG. 4 (Prior Art) is an enlarged, fragmentary, perspective detail of the distal end portion of the known instrument of FIGS. 1 and 2.
Figure 5:
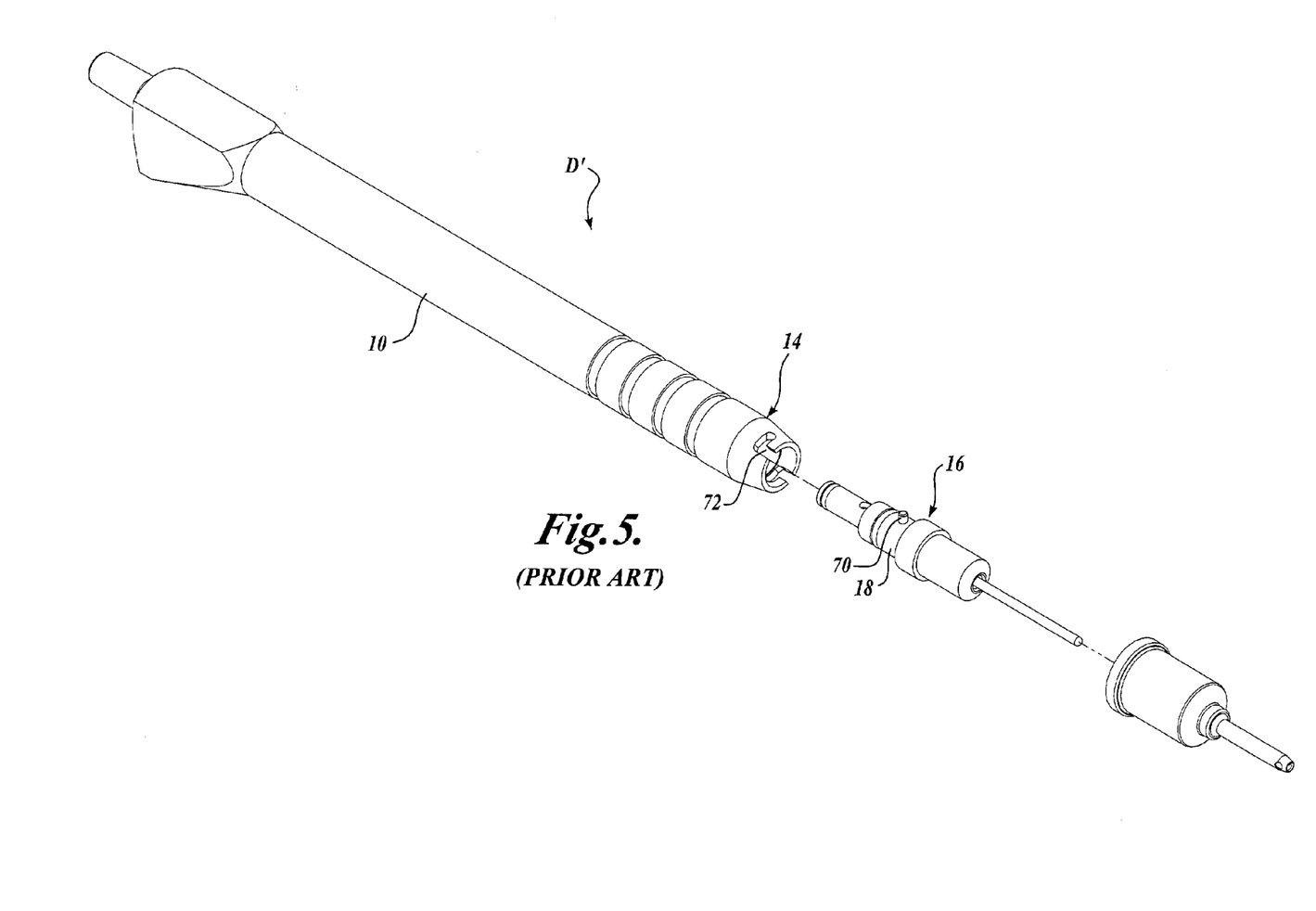
FIG. 5 (Prior Art) is a top perspective of a second known I/A instrument with parts shown in exploded relationship.

FIGS. 1–4 illustrate a first type of known I/A device D designed for use during cataract surgery. FIG. 1 shows three primary components in exploded relationship, namely, a handpiece 10 having a proximate end portion 12 and distal end portion 14, an I/A tip 16 having a proximate stem portion or hub 18 for insertion into the distal end portion 14 of the handpiece and a distal aspiration cannula 20, and a sleeve 22 insertable over the cannula 20 for dispersing irrigation liquid. These components are shown assembled and in longitudinal section in FIG. 2. FIGS. 3 and 4 are enlarged perspectives of the proximate and distal end portions, respectively, with the parts shown in section.

As best seen in FIG. 3, the proximate end portion 12 of the handpiece 10 includes a hollow hub 24 forming an aspiration port 26 for connection to a vacuum source, and a hollow inclined branch 28 forming an aspiration port 30 for connection to a source of irrigation liquid. Port 26 communicates with the long and straight central aspiration bore 32 of the instrument that extends longitudinally thereof all the way to the distal end portion 14 of the instrument shown in FIG. 4. Similarly, port 30 communicates with an annular channel 34 that encircles the bore 32 and is separated therefrom by a cylindrical wall 36. As seen in FIG. 4, wall 36 terminates at a distal end 38 which is recessed with respect to the distal end 40 of the outer wall 42 of the handpiece. Such handpiece outer wall includes several segments which combine to define the outer periphery of the irrigation channel 34.

Still referring to FIG. 4, the hub 18 of the I/A tip 16 includes a proximate portion 44 that fits snugly within the distal end portion of the cylindrical wall 36 of the handpiece and is sealed therein by a friction fit. A more distal portion 46 of the hub 18 is sized and designed to fit within the distal end portion of the handpiece outer wall 42. The I/A tip is manually insertable into and removable from the handpiece, the friction fit seals being achieved by O-rings 48 and 50. The cannula 20 of the I/A tip 16 is formed by a thin walled tube that extends lengthwise through the hub 18, including a proximate portion 52 which is secured within the proximate portion 44 of the hub and which communicates with an axial bore 54 that opens into the aspiration passage 32 of the handpiece. Thus, reduced pressure applied at the end port 26 is conveyed by way of aspiration passage 32 and bore 54, through the central bore 56 of the cannula 20, all the way to one or more ports located at the distal end portion 58 of the cannula.

The sleeve 22 includes a hub portion 62 that connects to the distal end portion 60 of the I/A tip 16. For example, these parts can connect by a threaded fit. The distal portion 64 of the sleeve surrounds the cannula 20 and has one or more end or side ports for ejecting irrigation liquid. Such liquid flows through the irrigation port 30 and annular passage 34, then inward through side ports 66 of the hub 18 to a smaller annular passage 68 around the cannula 20. Passage 68 opens into the sleeve 22 so that irrigation liquid is free to flow through the distal portion 64 of the sleeve for ejection through the end or side ports.

Figure 6:
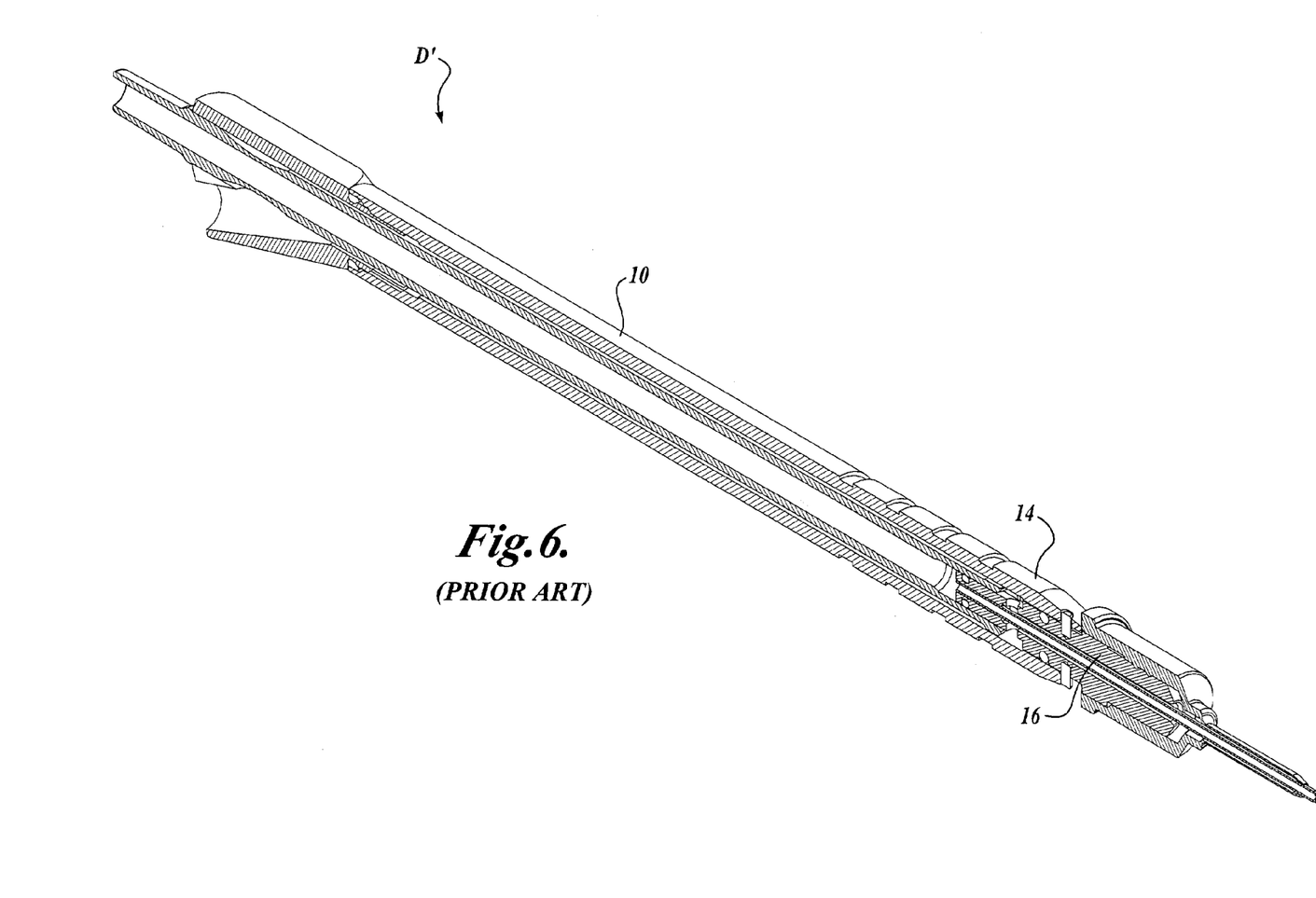
FIG. 6 (Prior Art) is a top perspective corresponding to FIG. 5, but with parts assembled and shown in section.
Figures 7, 8:
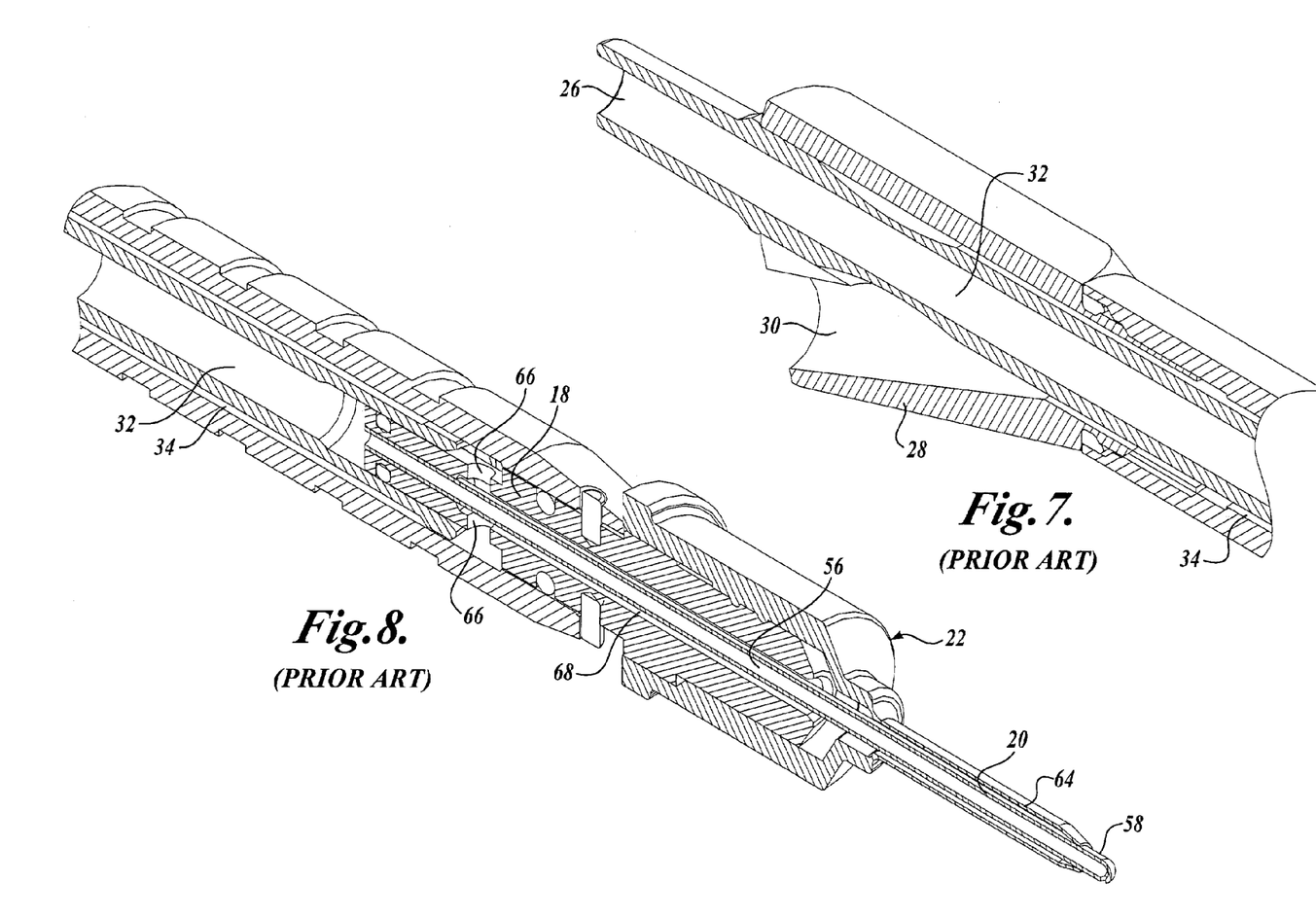
FIG. 7 (Prior Art) is an enlarged, fragmentary, perspective detail of the proximate end portion of the known instrument of FIGS. 5 and 6.
FIG. 8 (Prior Art) is an enlarged, fragmentary, perspective detail of the distal end portion of the known instrument of FIGS. 5 and 6.

A second known type of I/A device D' is illustrated in FIGS. 5–8, which correspond to FIGS. 1–4. The primary difference between device D' and device D is that device D' includes a bayonet latch for connecting the I/A tip 16 to the distal end portion 14 of handpiece 10. Such latch consists of pins 70 that project from the stem portion or hub 18 of the I/A tip 16 and fit within contoured slots 72 of the handpiece. Thus, a more positive lock of the I/A tip in the handpiece is provided. In other respects, the structure and functioning of the bayonet latch I/A tip is the same as for the tip previously described. With reference to FIGS. 7 and 8, suction applied at the handpiece end port 26 is conveyed by way of the axial bore 32 through the bore 56 of the cannula 20 to one or more end or side ports at the distal end or end portion 58. Irrigation liquid supplied through the inclined branch 28 is conveyed by way of the proximate port 30 and annular passage 34 to the side ports 66 of the hub 18, to the smaller annular passage 68 alongside the cannula. From there the irrigation liquid flows through the sleeve 22 to an end and/or side port in the cylindrical distal sleeve segment 64 that surrounds the cannula.

Devices D and D' correspond to I/A instruments available from MicroSurgical Technology, Inc., of Redmond, Wash.

FIGS. 9–12 illustrate a first embodiment of the present invention that enables tips of other manufacturers, such as specialized tips available from Alcon Laboratories, Inc., of Fort Worth, Tex., to be used with handpieces D of the type shown in FIGS. 1–4 (a second embodiment of the present invention allows such specialized aspiration tips to be used with handpieces D' of the type shown in FIGS. 6–8).

With reference to FIGS. 9–12, handpiece 10 and sleeve 22 are identical to the corresponding parts shown and described with reference to FIGS. 1–4. Aspiration tip 80 is of the construction used by Alcon Laboratories. Such tip includes a hollow, long, straight distal portion or cannula 82, an externally threaded hub 84, and an intermediate hub 86 which may have flat sides adapted for reception in a wrench-like instrument used to rotate the tip for coupling it to an Alcon Laboratories handpiece.

Figures 11, 12:
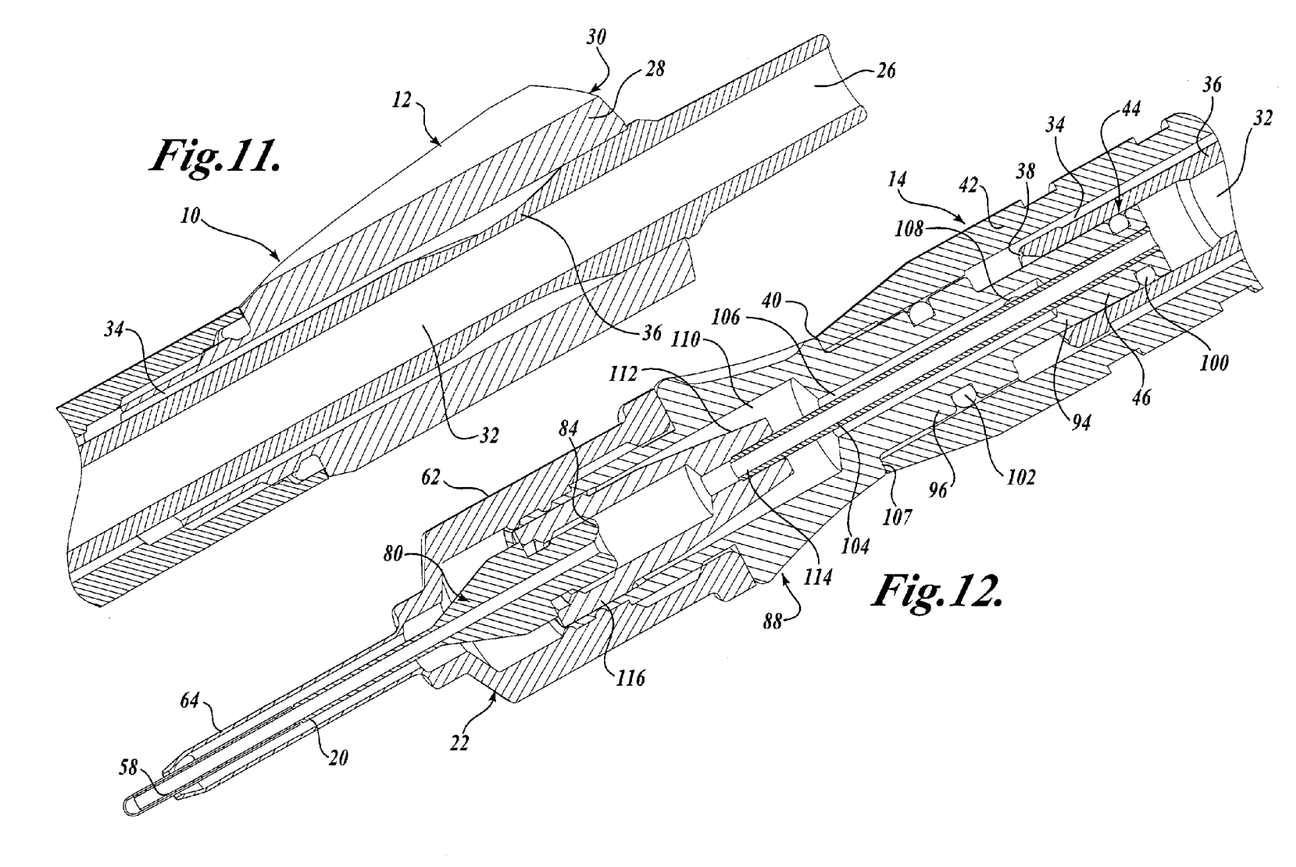
FIG. 11 is an enlarged, fragmentary, perspective detail of the proximate end portion of the instrument of FIG. 9 and FIG. 10, with the parts shown in section.
FIG. 12 is an enlarged, fragmentary, perspective detail of the distal end portion of the instrument of FIGS. 9 and 10, including the connector in accordance with the present invention, with the parts shown in section.

In accordance with the present invention, a special connector 88 is provided which has a proximate stem portion or hub 90 coupled to the Microsurgical Technologies handpiece 10, and a distal portion 92 for coupling to the Alcon Laboratories aspiration tip 80 and the conventional irrigation sleeve 22. These parts are shown assembled and in longitudinal cross-section in FIG. 10. FIGS. 11 and 12 are enlarged perspectives of the proximate and distal portions, respectively, of the modified instrument using the connector 88, with parts shown in section.

With reference to FIG. 11, the proximate end portion 12 of the handpiece 10 is identical to that previously described. In FIG. 11, the branch 28 containing the irrigation port is positioned away from the viewer but communicates with the annular irrigation passage 34.

With reference to FIG. 12, the distal end portion 14 of the handpiece 10 includes the outer wall 42 terminating at its distal end 40 and the inner wall 36 terminating at its distal end 38. The inner wall 36 defines the central aspiration bore 32. The annular space 34 between the inner wall 36 and outer wall 42 defines the passage for irrigation liquid.

Figures 9, 9A:
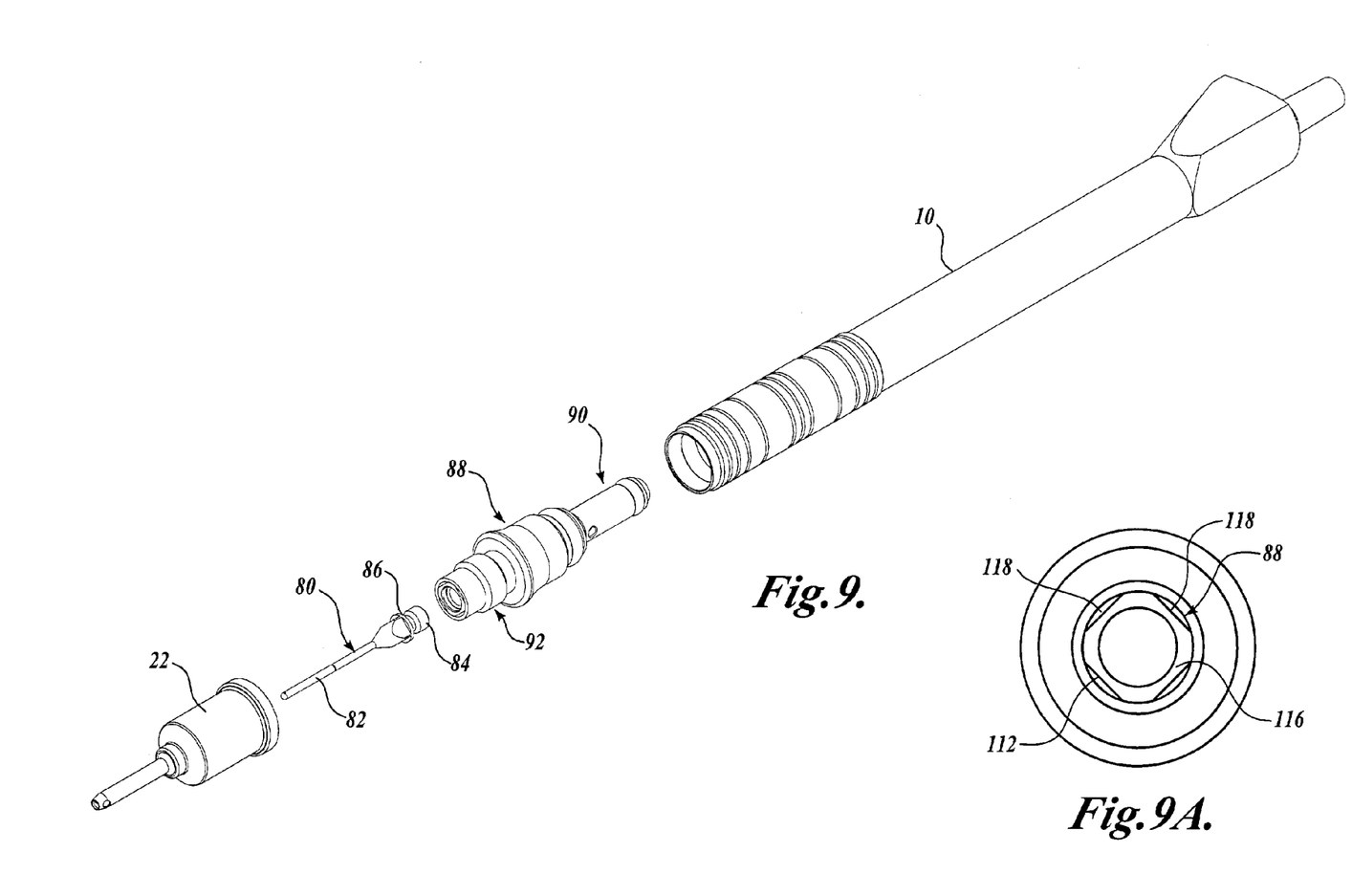
FIG. 9 is a perspective of an I/A instrument having a connector in accordance with the present invention, with parts shown in exploded relationship.
FIG. 9A is an enlarged end elevation of the connector.
Figure 10:
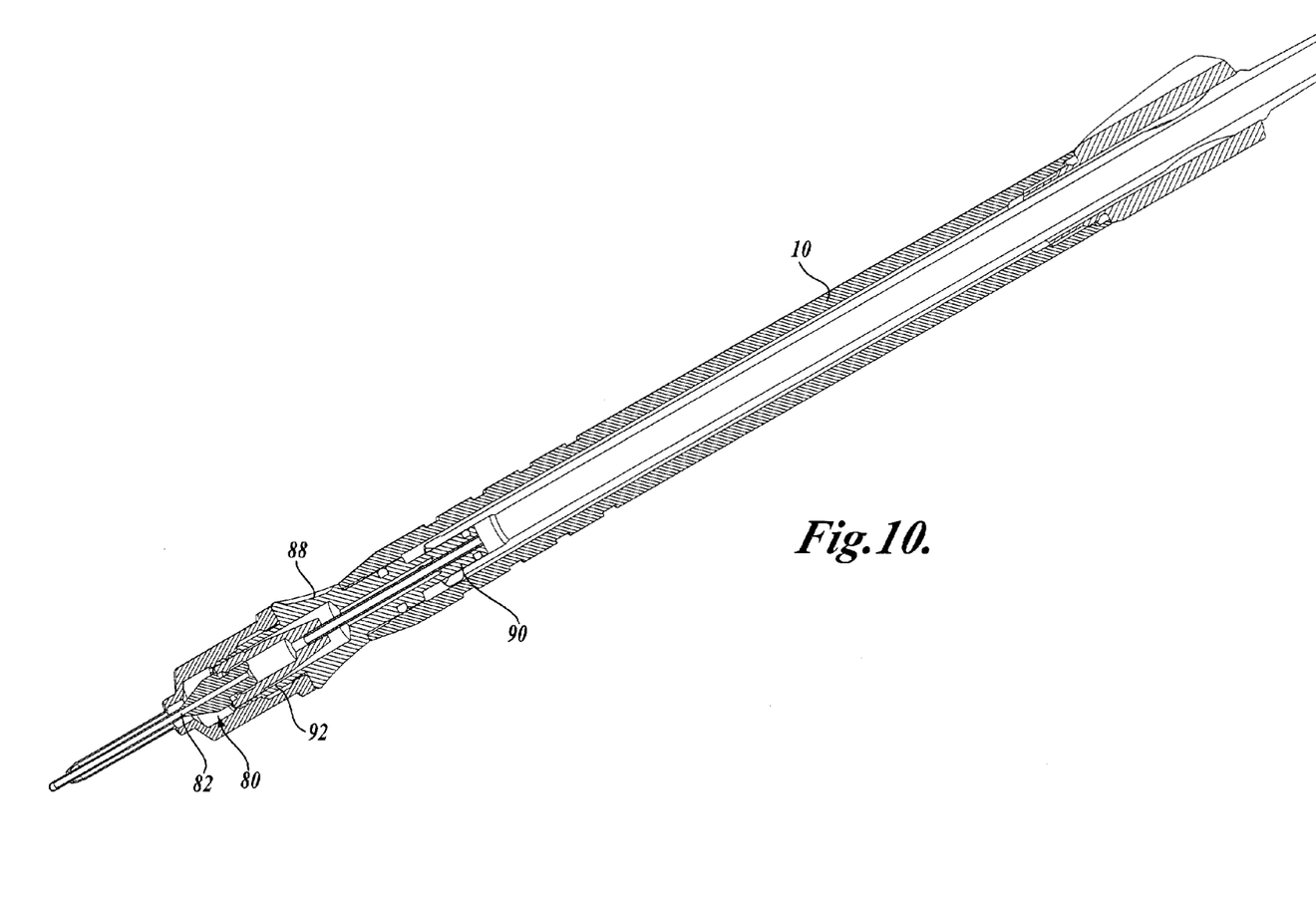
FIG. 10 is a perspective corresponding to FIG. 9, but with the parts assembled and shown in section.

Connector 88, manually separable from the handpiece, in accordance with the present invention, has a proximate stem portion or hub 94 of a first diameter sized to fit snugly within the distal end portion of the inner wall 36. Moving distally, connector 88 includes a second stem portion or hub 96 that fits snugly within the distal end portion of the outer wall 42. O-rings 100 and 102 provide tight, sealing, friction fits. A central aspiration tube 104 has a proximate end portion secured in the first connector hub 94. A shoulder 107 limits the insertion of the connector into the handpiece by engagement against the distal end 40 of the outer wall 42. An annular chamber 106 is formed around the central portion of the aspiration tube 104, communicating with the irrigation passage 34 by way of one or more side ports 108. The narrow annular irrigation passage 106 opens distally into a wider chamber 110. This chamber is generally cylindrical and can be machined into the body of the connector from its distal end. A tapered insert 112 is secured in the chamber 110, with a central aspiration bore 114 communicating with the aspiration tube 104. The distal portion of the aspiration chamber 114 is enlarged and has internal threads that mate with external threads of the hub 84 of the aspiration tip 80. Thus, the aspiration tip 80, such as a tip designed for an Alcon Laboratories device, can be coupled to the connector 88, similar to the coupling of such a tip to an Alcon Laboratories handpiece. The distal end portion 116 of the insert 112 is not circular, but has an outer periphery with one or more openings that communicate with the irrigation liquid chamber 110 (this aspect is seen in FIGS. 9 and 9A). For example, in a preferred embodiment, the distal end portion of the insert 112 can be square, providing several flat sides 118 spaced inward from the body of the connector 88 to form passages for the flow of irrigation liquid therethrough. Such liquid passes to the interior of the sleeve 22, which can couple to the distal end portion of the connector, such as by a threaded fit.

Figures 13, 13A:
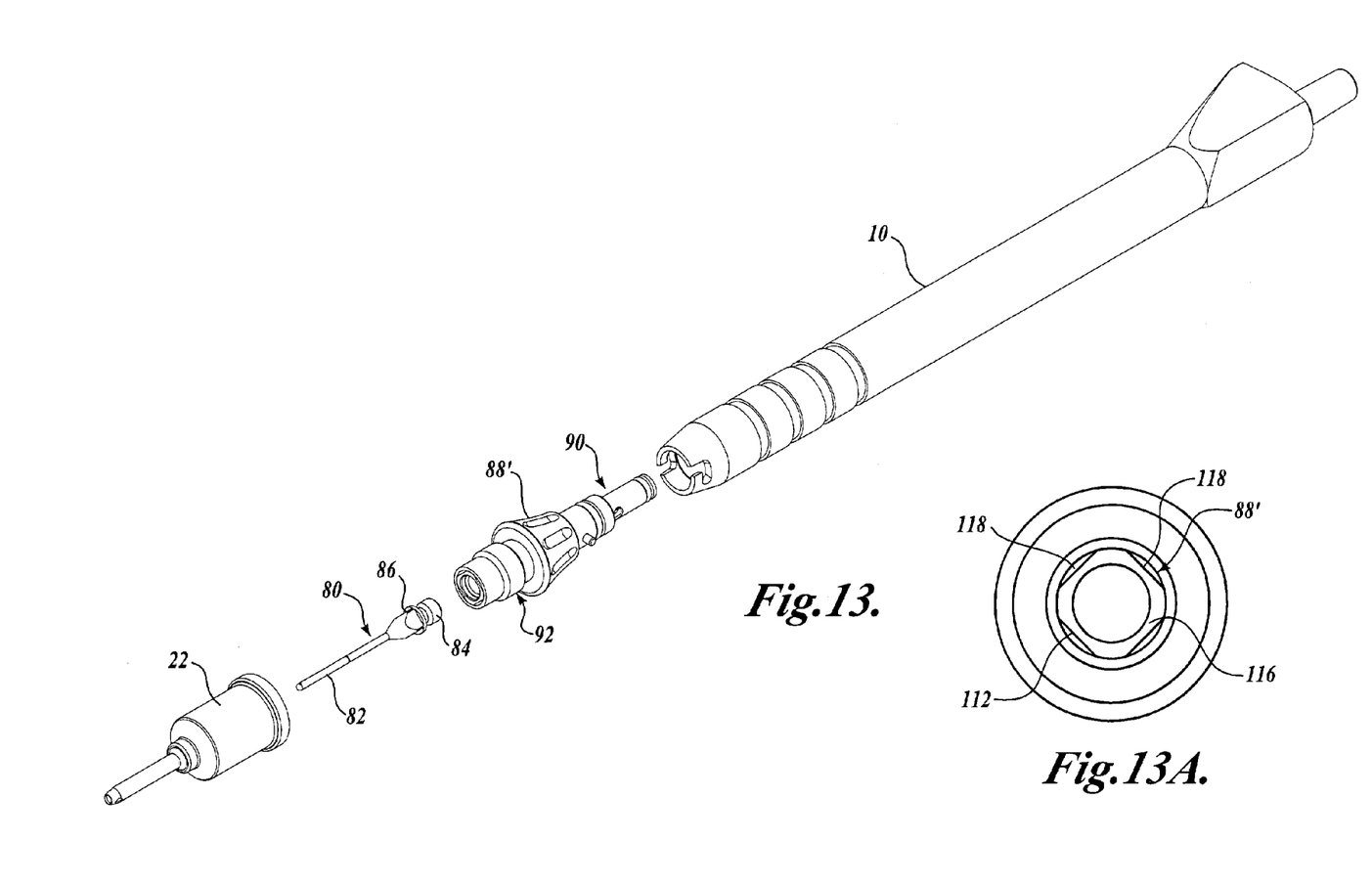
FIG. 13 is a perspective of an I/A instrument having a connector in accordance with the present invention, with parts shown in exploded relationship.
FIG. 13A is an enlarged end elevation of the connector.
Figure 14:
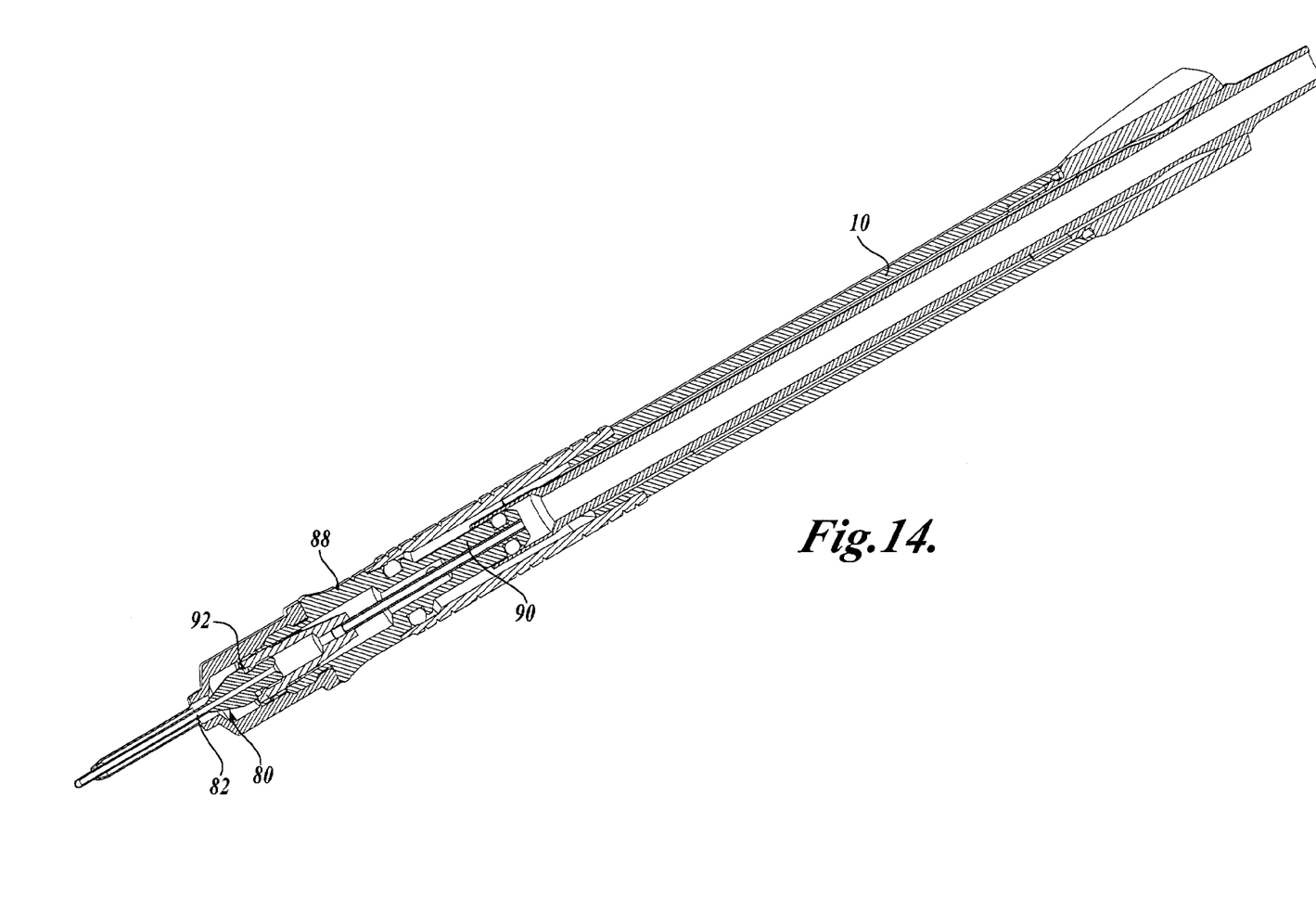
FIG. 14 is a perspective corresponding to FIG. 13, but with the parts assembled and shown in section.
Figures 15, 16:
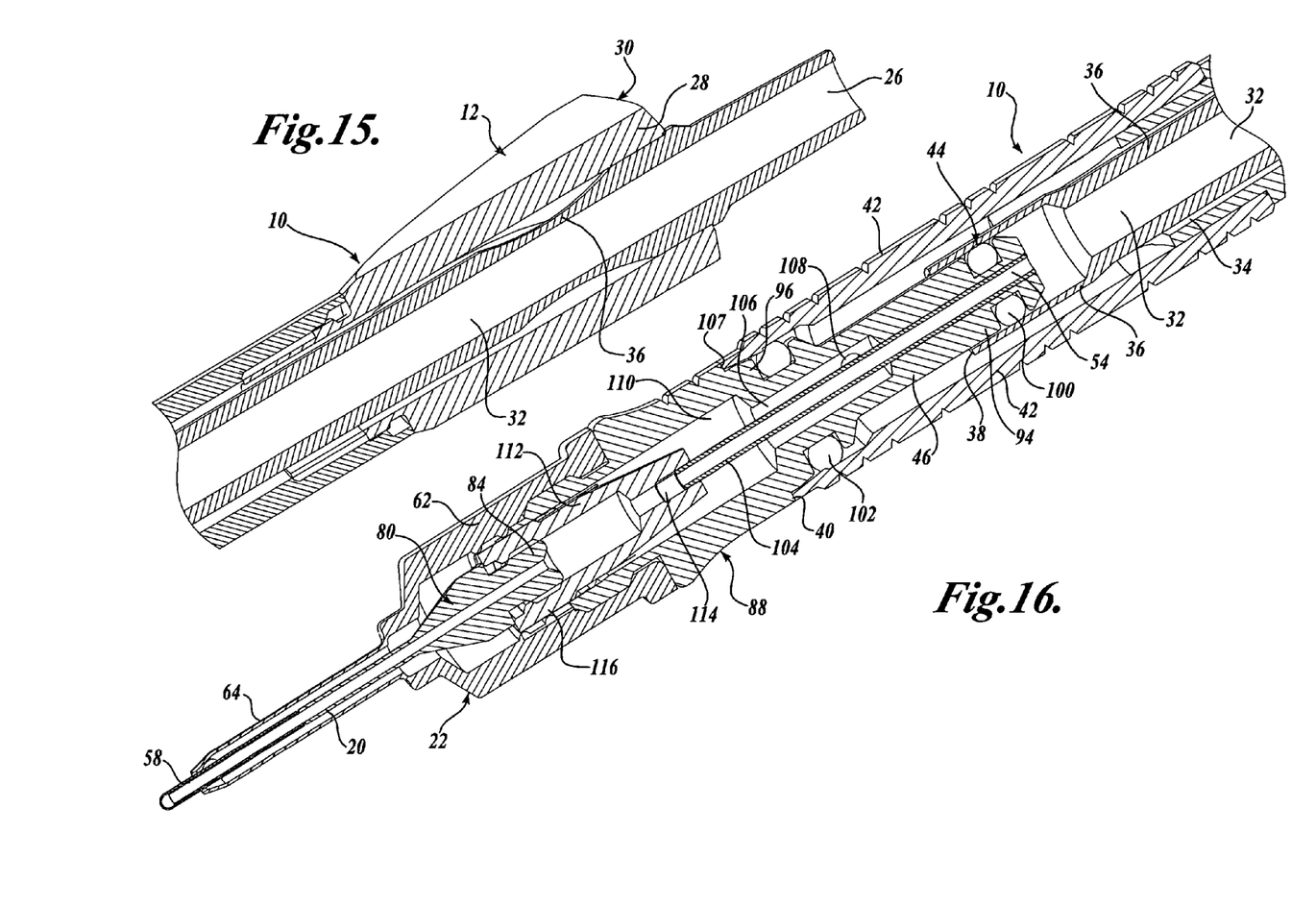
FIG. 15 is an enlarged, fragmentary, perspective detail of the proximate end portion of the instrument of FIG. 13 and FIG. 14, with the parts shown in section.
FIG. 16 is an enlarged, fragmentary, perspective detail of the distal end portion of the instrument of FIGS. 13 and 14, including the connector in accordance with the present invention, with the parts shown in section.

FIGS. 13–16 correspond to FIGS. 9–12, respectively, illustrating a second embodiment of connector 88' that will couple to a MicroSurgical Technologies handpiece 10 of the type described above with reference to FIGS. 5–8 (the bayonet latch handpiece). Other than the shape of the central portion, the provision of latch pins 120, and dimensioning to fit the modified handpiece, the construction of connector 88' is identical to the construction of connector 88, previously described, and like parts are numbered the same in FIGS. 13–16 as for the embodiment of FIGS. 9–12. With reference to FIG. 16, connector 88, manually separable from the handpiece, has the narrower proximate stem portion or hub 94 sized to fit snugly within the distal end portion of the inner wall 36. The second stem portion or hub 96 fits snugly within the distal end portion of the outer wall 42. O-rings 100 and 102 provide tight, sealing, friction fits. The proximate end portion of the central aspiration tube 104 is secured in the first connector hub 94. Shoulder 107 limits the insertion of the connector 88' into the handpiece 10 by engagement against the distal end 40 of the outer wall 42. Annular chamber 106 is formed around the central portion of the aspiration tube 104, communicating with the irrigation passage 34 by way of one or more side ports 108. The narrow annular irrigation passage 106 opens distally into the larger chamber 110. The tapered insert 112 is secured in the chamber 110, with the central aspiration bore 114 communicating with the aspiration tube 104. The distal portion of the aspiration chamber 114 is enlarged and has internal threads that mate with external threads of the hub 84 of the aspiration tip 80. Thus, the separate aspiration tip 80, such as a tip designed for an Alcon Laboratories device, can be coupled to the connector 88'. The distal end portion 116 of the insert 112 has the outer periphery with one or more openings that communicate with the irrigation liquid chamber 110, as seen in FIGS. 13 and 13A. For example, the distal end portion of the insert 112 can be square, providing the several flat sides 118 spaced inward from the body of the connector 88' to form passages for the flow of irrigation liquid therethrough. Such liquid passes to the interior of the sleeve 22, which can couple to the distal end portion of the connector, such as by a threaded fit.

While the preferred embodiments of the invention has been illustrated and described, it will be appreciated that various changes can be made therein without departing from the spirit and scope of the invention.

The embodiments of the invention in which an exclusive property or privilege is claimed are defined as follows:

1. A medical instrument comprising:
   a handpiece having:
      a proximate end portion;
      a distal end portion;
      an aspiration port for connection to a low pressure source for aspiration through the aspiration port;
      an irrigation port for connection to a source of irrigation liquid for flow of irrigation liquid through the irrigation port;
      an inner wall having a distal end and a bore forming an aspiration channel extending from the first port and having an opening at the inner wall distal end;
      an outer wall surrounding the inner wall and forming an irrigation channel between the inner wall and the outer wall which irrigation channel extends from the second port and has an opening at the outer wall distal end;
   a separate connector constructed and arranged so as to be manually separable from the handpiece and having:
      a proximate end portion;
      a distal end;
      an aspiration channel extending through the connector from the proximate end portion thereof to the distal end thereof;
      an irrigation channel extending through the connector from the proximate end portion thereof to the distal end portion thereof;
      a stem on the connector proximate end portion adapted to be manually coupled to the distal end portion of the handpiece with the connector aspiration channel forming a continuation of the handpiece aspiration channel and the connector irrigation channel forming a continuation of the handpiece irrigation channel and the stem fitted within a distal end portion of the handpiece outer wall;
   a separate aspirator tip component having:
      a proximate end portion;
      a distal end portion;
      an aspiration channel extending through the tip component from the proximate end portion to the distal end portion;
      a stem on the tip component proximate end portion adapted to be coupled on to and uncoupled from the distal end of the connector with the tip component aspiration channel forming a continuation of the connector aspiration channel.

2. The instrument defined in claim 1, the separate aspiration tip component stem fits within the distal end of the connector aspiration channel, the connector irrigation channel opening at one or more locations around the distal end of the connector for flow of irrigation liquid along the outside of the tip component.

3. The instrument defined in claim 1, in which the tip component is removably coupled to the connector by a threaded connection.

4. The instrument defined in claim 3, in which the stem of the connector is adapted to be manually coupled to the distal end portion of the handpiece by a sliding friction fit.

5. The instrument defined in claim 4, in which the stem of the connector and the distal end portion of the handpiece have a bayonet latch for retaining the connector on the handpiece.

6. The instrument defined in claim 1, in which the handpiece has a central aspiration tube including a bore forming the handpiece aspiration channel, the outer wall being spaced outward from the aspiration tube and defining an annular passage forming the irrigation channel, the outer wall extending distally beyond the aspiration tube, and the stem of the connector having a first portion coupled by a friction fit against the aspiration tube and a second portion coupled by a friction fit against the outer wall, the first connector stem portion having a diameter less than the diameter of the second connector stem portion.

7. The instrument defined in claim 6, in which the connector stem portion has a shoulder limiting insertion of the connector into the handpiece by butting against the distal end of one of the handpiece walls.

8. The instrument defined in claim 1, in which the connector irrigation channel has one or more side ports opening into the irrigation channel of the handpiece, an aspiration tube extending lengthwise of the connector from the proximate end portion thereof through a proximate portion of the connector irrigation channel, the irrigation channel having an enlarged chamber of a size greater than the size of a proximate portion of the irrigation channel, and the connector having an insert fitted within the chamber, coupled to the aspiration tube and defining passages and openings for the connector irrigation channel at the distal end portion of the connector.

9. The instrument defined in claim 8, in which the tip component is threadedly coupled to the distal end portion of the connector insert.

* * * * *

UNITED STATES PATENT AND TRADEMARK OFFICE
CERTIFICATE OF CORRECTION

PATENT NO. : 6,887,221 B1
DATED : May 3, 2005
INVENTOR(S) : J. M. Baillargeon et al.

It is certified that error appears in the above-identified patent and that said Letters Patent is hereby corrected as shown below:

Column 6,
Line 10, "end portion thereof;" should read -- end thereof; --.

Signed and Sealed this

Tenth Day of January, 2006

JON W. DUDAS
*Director of the United States Patent and Trademark Office*